United States Patent [19]

Oki et al.

[11] 4,357,223
[45] Nov. 2, 1982

[54] OXYGEN SENSING DEVICE

[75] Inventors: Shuichiro Oki, Aichi; Syunzo Mase, Tobishima, both of Japan

[73] Assignee: NGK Insulators Ltd., Nagoya, Japan

[21] Appl. No.: 158,902

[22] Filed: Jun. 12, 1980

[30] Foreign Application Priority Data

Jun. 26, 1979 [JP] Japan .................... 54-86530[U]

[51] Int. Cl.$^3$ ............................ G01N 27/58
[52] U.S. Cl. .................................. 204/195 S
[58] Field of Search ...................... 204/195 S, 1 S

[56] References Cited

U.S. PATENT DOCUMENTS

| 3,841,987 | 10/1974 | Friese et al. | 204/195 S |
| 4,076,608 | 2/1978 | Fujishiro et al. | 204/195 S |
| 4,253,302 | 3/1981 | Asano et al. | 204/195 S X |

FOREIGN PATENT DOCUMENTS 54-17414  2/1979  Japan ..................... 204/195 S Primary Examiner—G. L. Kaplan
Attorney, Agent, or Firm—Stevens, Davis, Miller and Mosher

[57] ABSTRACT

An oxygen sensing device in which a tubular solid electrolyte, one end of which is closed, is applied with electrodes on the outer and inner surfaces, the closed end side of the solid electrolyte is exposed to combustion gases exhausted from internal combustion engines, the inner electrode and the outer electrode are contacted with ambient air and the combustion gases respectively, is characterized in that an inner surface of a tubular solid electrolyte is constructed of a wide opening portion, a first diameter reducing portion connecting to said wide opening portion, an intermediate wide opening portion having a uniform diameter which is smaller than the wide opening portion, and connecting to the first diameter reducing portion, a second diameter reducing portion connecting to the intermediate wide opening portion and a narrow opening portion connecting to the second diameter reducing portion which extends to the closed end.

1 Claim, 5 Drawing Figures

OXYGEN SENSING DEVICE

The present invention relates to an oxygen sensing device for measuring oxygen concentration in combustion gases exhausted from internal combustion engines by means of an oxygen concentration cell composed of a solid electrolyte.

An oxygen sensing device which precisely controls the air-fuel ratio by measuring the concentration of oxygen in combustion gases exhausted from automotive internal combustion engines by means of an oxygen concentration cell composed of oxygen ion conductive solid electrolyte, such as zirconia and the like, has been known. For such an oxygen sensing device, a solid electrolyte having the structure as shown in FIG. 1 has been heretofore generally used. That is, a tubular solid electrolyte 1, one end of which is closed, is provided with a wide opening portion 2 where an inner electrode 11 connects with a metallic terminal 7 through a flexible conductive material 6. A diameter reducing portion 3 is provided at the open end, and a narrow opening portion 5 having a uniform inner diameter, extends from the portion 3 to the closed end 4. This solid electrolyte 1 has electrodes 11 and 12 on the inner surface. The outer surface and the inner electrode 11 is electrically connected with the metallic terminal 7 by inserting an annular flexible conductive material 6 at the wide opening portion 2 and the portion 3. Thus, the metallic terminal 7 must have such a form that outer surfaces of a top end portion 8 and a central portion 9 contact against inner surfaces of the narrow opening portion 5 and the wide opening portion 2 respectively. However, the outer diameters of the top end portion 8 and the central portion 9 are in reality made to be smaller than the inner diameters of the narrow opening portion 5 and the wide opening portion 2 of the solid electrolyte 1 respectively due to the shrinkage of the solid electrolyte when firing and the variation in precision of the metallic terminal 7 and therefore there is some clearance between these members and it can not be avoided that a small amount of the flexible conductive material 6 falls down when assembling the oxygen sensing device or owing to vibration in an automotive vehicle. As the flexible conductive material 6, use is usually made of graphite and a little amount of graphite falls down to the closed end portion 4 when graphite is inserted in the wide opening portion 2 of the solid electrolyte 1 or owing to the vibration of an automotive vehicle.

The closed end portion 4 is the portion for detecting the oxygen concentration in the combustion gases and is heated, so that the graphite burns and oxygen at the closed end portion 4 is consumed and the oxygen partial pressure of the standard gas varies. But the outer diameter and the inner diameter of the conventional solid electrolyte at the detecting portion are about 8 mm and 5 mm respectively and the inner diameters of the wide opening portion 2 and the narrow opening portion 5 are about 8 mm and 5 mm respectively and the inner diameter of the hollow portion 10 of the metallic terminal 7 can be made relatively large, about 4 mm, so that the standard gas can easily pass through the hollow portion 10 and fresh air can always be supplied to the closed end portion 4 and the oxygen sensing device can be normally operated. However, when the diameter of the solid electrolyte is made smaller in order to improve the thermal shock resistance and the operation time in cold starts, for example, when the outer diameter of the detecting portion is 4 mm, the inner diameter of the closed end portion 4 is 2 mm, the diameter of the wide opening portion 2 is 4 mm and the diameter of the narrow opening portion 5 is 2 mm, and the diameter of the hollow portion 10 of the metallic terminal 7 becomes 1 mm in order to ensure the mechanical strength of the metallic terminal 7. If a little amount of graphite of the flexible conductive material falls down to the closed end portion 4 when graphite is inserted in the wide opening portion 2 or owing to vibration of automotive vehicle, and burns and the oxygen partial pressure of the standard gas varies, but the diffusion of fresh air is slow, because the diameter of the hollow portion 10 is small and for example, as shown in FIG. 2, a long time is necessary to obtain normal operation of the oxygen sensing device. FIG. 2 shows the variation of the electromotive force with lapse of time measured by means of oxygen sensing devices wherein the inner diameters of the detecting portion are 2, 3 and 4 mm and the diameters of the hollow portion of the metallic terminal are 1, 2 and 3 mm respectively, when 5 mg of graphite falls down to the closed end portion. These data were obtained by exposing the oxygen sensing devices to environment (rich environment) of automotive combustion gas in which the fuel is in excess, at 600° C. for a long time. The metallic terminal 7 is preferred to have a thickness of more than 0.5 mm in order to maintain its practical strength. Furthermore, in the case where the inner diameter of the detecting portion is smaller, the shape of the flexible conductive material is small and the volume of the portion for leading out the inner electrode is small, so that the contacting area is small and the reliability of the electric conductivity is poor.

The present invention has been made in order to solve the above described drawbacks.

A structure for an oxygen sensing device by which stable operation is obtained, wherein the diameter of the solid electrolyte is small and therefore the operation start-up is rapid and thermal shock resistance is high.

Another object of the present invention is to provide the structure in which reliability is high and assembly is easy.

A further object of the present invention is to provide a structure which does not cause deformation in a molding jig when the tubular solid electrolyte having a closed end is produced.

For better understanding of the invention, reference is taken to the accompanying drawings, wherein.

Figure 1:
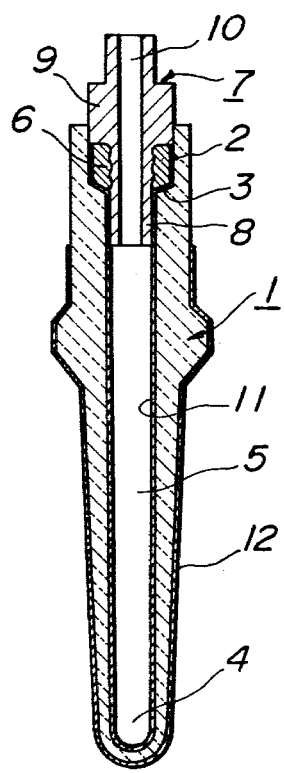
FIG. 1 is a cross sectional view of one embodiment of a solid electrolyte used for a conventional oxygen sensing device.
Figure 2:
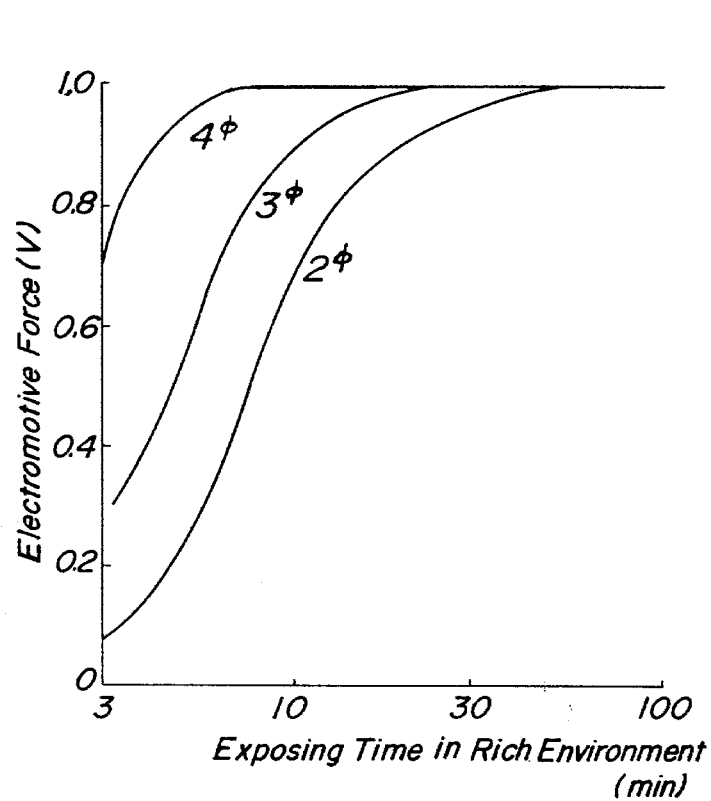
FIG. 2 is a graph showing variation of electromotive force with lapse of time when the inner diameter of the detecting portion of the conventional solid electrolyte is varied.
Figure 3:
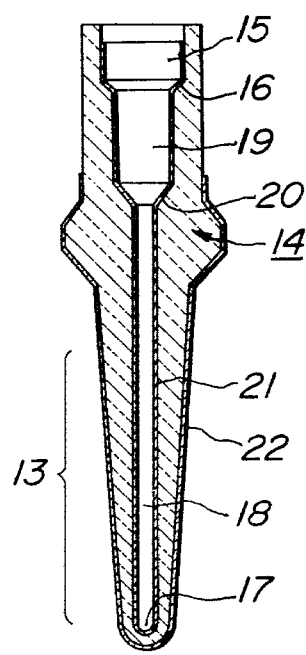
FIGS. 3 and 4 are cross sectional views of embodiments of solid electrolytes to be used for the oxygen sensing devices according to the present invention.
Figure 4:
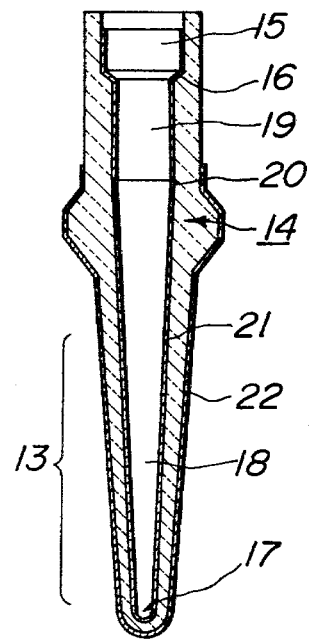

A detailed explanation will be made hereinafter with reference to FIG. 3 which is one embodiment of the present invention. A tubular solid electrolyte 14, having a closed end composed of zirconia and other substances, is provided with electrodes 21 and 22 at the inner surface and the outer surface. The inner diameter of the detecting portion 13 exposed to combustion gases is not greater than 3 mm. At the inner wall of the opening end side, a wide opening portion 15 is provided and a first diameter reducing portion 16 wherein a flexible conductive material leading out the inner electrode is inserted and held. There is also provided an intermediate opening portion 19 having a substantial uniform inner diameter, which is slightly smaller than that of the wide opening portion 15 and slightly larger than that of a narrow opening portion 18, at a center portion of the solid electrolyte 14, and a second diameter reducing portion 20 at the closed end side of the intermediate opening portion 19. The narrow opening portion 18 extending from the above described portion 20 to the closed end portion 17 may be of uniform diameter as shown in FIG. 3, or a tapered form in which the diameter becomes gradually smaller toward the closed end as shown in FIG. 4 or other forms. The detecting portion 13 of the solid electrolyte 14 is preferred to be 2~5 mm, more preferably 3~4 mm in the outer diameter and 1~3 mm, more preferably 1.5~2.5 mm in the inner diameter in order to improve thermal shock resistance. In order to improve the thermal shock resistance and to obtain the conductive reliability, at the openning end side of the solid electrolyte, the outer diameter is preferred to be 4~10 mm, more preferably 6~8 mm and the inner diameter at the wide opening portion 15 is preferred to be 4~6 mm, more preferably 4~5 mm. The intermediate opening portion 19 is preferred to be 2~5 mm, more preferably 3~4 mm in the inner diameter in order to make the diffusion of air easy. The average of the inner diameter of the narrow opening portion extending from the second diameter reducing portion 20 to the closed end 17 is desired to be more than 1/50 of the length of the narrow opening portion in order to make the diffusion of air easy.

Figure 5:
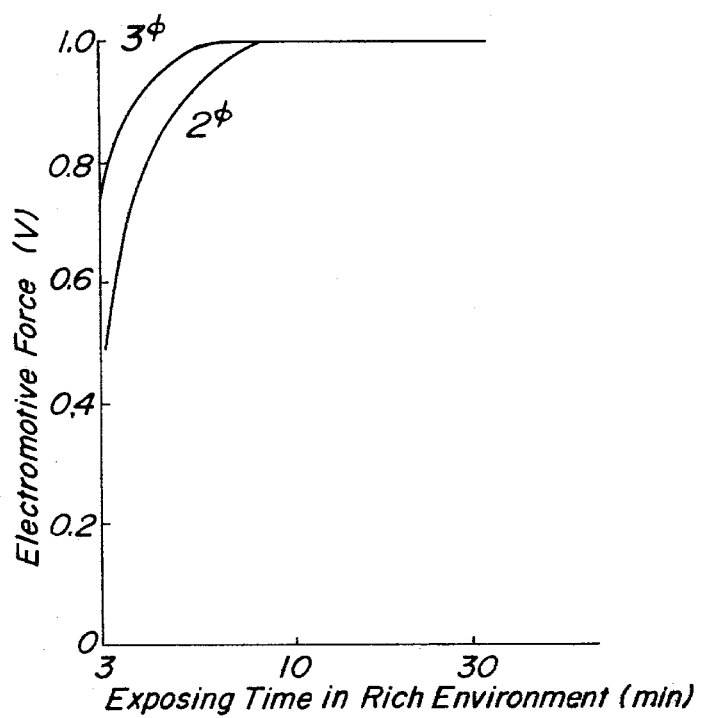
FIG. 5 is a graph showing variation of electromotive force of the oxygen sensing device according to the present invention.

The oxygen sensing device according to the present invention has the above described construction. The center portion 9 of the metallic terminal 7 is inserted into the wide opening portion 15 and the top end portion 8 is inserted into the intermediate opening portion 19, so that the diameter of the hollow portion 10 of the metallic terminal 7 can be enlarged. Even if the flexible conductive material 6 falls down into the closed end portion 17 when the oxygen sensing device is assembled or owing to the vibration of the automotive vehicle during driving and burns and the oxygen partial pressure of air which is the standard gas, varies, the normal electromotive force is recovered in a short time as shown in FIG. 5. Furthermore, since the diameter of the flexible conductive material 6 is enlarged, the reliability of the conductivity of the oxygen sensing device at its connection of the electrode after assembly is high and the handling of the conductive material upon assembly is easy. In addition, the deformation of the core when hydrostatic pressure generally used upon molding of the solid electrolyte hardly occurs and molding is easily conducted.

As mentioned above, the oxygen sensing device according to the present invention not only operates normally but also can improve the yield and the reliability and is particularly useful as an oxygen sensing device in combustion gases of automotive vehicles and the like and serves to achieve efficient use of fuel and to decrease combustion gas, a public nuisance, and is very useful commercially.

What is claimed is:

1. An oxygen sensing device having a tubular solid electrolyte, said tubular solid electrolyte having an open end and a closed end, said open end having a metallic terminal attached thereto, said tubular solid electrolyte having electrodes on the outer and inner surfaces thereof, said inner electrode being connected with said metallic terminal through a flexible conductive material, the closed end side of the solid electrolyte being exposed to combustion gases exhausted from internal combustion engines, the inner electrode and outer electrode being contacted with ambient air and the combustion gases respectively, and oxygen partial pressure in the combustion gases being measured by utilizing the principle of an oxygen concentration cell, the inner surface of the tubular solid electrolyte having a first diameter reducing portion connecting to a wide opening portion, which forms a portion leading out the inner electrode, an intermediate wide opening portion having a substantial uniform diameter smaller than that of the above described wide opening portion, a second diameter reducing portion connecting to the intermediate wide opening portion and a narrow opening portion, said narrow opening portion having a smaller diameter than the intermediate wide opening portion, which extends to the closed end, said wide opening portion, said first diameter reducing portion, said intermediate wide opening portion, said second diameter reducing portion and said narrow opening portion being arranged toward the closed end from the opening end side of the tubular solid electrolyte in said order, an average inner diameter of said narrow opening portion being not greater than 3 mm and wherein the flexible conducting material is graphite.

* * * * *